(12) United States Patent
Williams

(10) Patent No.: US 10,937,525 B2
(45) Date of Patent: Mar. 2, 2021

(54) SYSTEM THAT GENERATES PHARMACOKINETIC ANALYSES OF OLIGONUCLEOTIDE TOTAL EFFECTS FROM FULL-SCAN MASS SPECTRA

(71) Applicant: BioTune Computations LLC, La Habra, CA (US)

(72) Inventor: Renee Williams, La Habra, CA (US)

(73) Assignee: BioTune Computations LLC, La Habra, CA (US)

( * ) Notice: Subject to any disclaimer, the term of this patent is extended or adjusted under 35 U.S.C. 154(b) by 0 days.

(21) Appl. No.: 16/911,038

(22) Filed: Jun. 24, 2020

(65) Prior Publication Data

US 2020/0402617 A1 Dec. 24, 2020

Related U.S. Application Data

(60) Provisional application No. 62/865,327, filed on Jun. 24, 2019.

(51) Int. Cl.
| | | |
|---|---|---|
| *G16B 40/10* | (2019.01) | |
| *G16B 30/00* | (2019.01) | |
| *C12Q 1/6872* | (2018.01) | |

(52) U.S. Cl.
CPC .......... *G16B 40/10* (2019.02); *C12Q 1/6872* (2013.01); *G16B 30/00* (2019.02)

(58) Field of Classification Search
None
See application file for complete search history.

(56) References Cited

U.S. PATENT DOCUMENTS

| | | |
|---|---|---|
| 6,238,871 B1 | 5/2001 | Koster |
| 6,906,320 B2 | 6/2005 | Sachs et al. |
| 2004/0181347 A1 | 9/2004 | Yoshinari et al. |
| 2018/0011990 A1 | 1/2018 | Moseley et al. |

OTHER PUBLICATIONS

Studzińska, Sylwia. "Review on investigations of antisense oligonucleotides with the use of mass spectrometry." Talanta 176 (2018) : 329-343.*

* cited by examiner

*Primary Examiner* — G Steven Vanni
(74) *Attorney, Agent, or Firm* — Arc IP Law, PC; Joseph J. Mayo

(57) ABSTRACT

System that automates analysis of mass spectrometry data for oligonucleotides to generate pharmacokinetic parameters and models. A user inputs an oligonucleotide sequence and a maximum number of nucleotides that may be lost during metabolism while retaining therapeutic effectiveness. The system calculates the possible active metabolites and develops a mass spectrum filter for the mass-to-charge ratio of ions for these metabolites. Full-scan spectra are analyzed to calculate the total concentration of these active molecules present in a time series of samples. Pharmacokinetic models and parameters are calculated from the time series of total concentration. Because full-scan spectra are captured, assumptions may be modified and analyses may be quickly rerun without collecting additional data. Overall pharmacokinetic analysis is therefore much more streamlined and efficient, reducing cost, delay, and the need for a mass spectrometrist who is highly skilled in spectral analysis.

8 Claims, 7 Drawing Sheets

US 10,937,525 B2

SYSTEM THAT GENERATES PHARMACOKINETIC ANALYSES OF OLIGONUCLEOTIDE TOTAL EFFECTS FROM FULL-SCAN MASS SPECTRA

This patent application claims the benefit of U.S. Provisional Patent Application Ser. No. 62/865,327, filed 24 Jun. 2019, the specification of which is hereby incorporated herein by reference.

BACKGROUND OF THE INVENTION

Field of the Invention

One or more embodiments of the invention are related to the fields of analytical chemistry and data processing. More particularly, but not by way of limitation, one or more embodiments of the invention enable a system that generates pharmacokinetic analyses of oligonucleotide total effects from full-scan mass spectra.

Description of the Related Art

Mass spectrometry (MS) is a powerful tool for analyzing the molecular composition of biological samples. It is especially useful in the drug discovery process for assessing the movement of a drug through the body with respect to characterizing absorption, distribution, bioavailability, metabolism, and excretion as a function of time. Such pharmacokinetics (PK) analysis is required for all drugs before moving from research and development to clinical trials and, potentially, the market.

MS is a powerful tool to sequence DNA (U.S. Pat. No. 6,238,871 B1) due to its high detection sensitivity and accuracy of mass measurements. In U.S. Pat. No. 6,238,871, Koster et. al. employs MS to analyze Sanger sequencing reaction mixtures, where four families of chain-terminated fragments of the DNA are obtained prior to the MS analysis.

MS data analysis techniques have been employed to identify analytes and determine their abundances in different samples (U.S. Pat. No. 6,906,320 B2). In this example, Sachs et. al. detects peptide changes in different samples by determining statistically significant changes in m/z-intensity peaks from the spectrum of each sample. This method is particularly useful for the qualitative study of complex biological samples, but it can also be used for quantitative analysis when calibration curves are obtained.

In the research and development of biomolecules for the drug development process, quantitative information is pivotal for determining the kinetic parameters of a drug candidate. Conventional methods for determining the PK profiles of molecules rely on integrating peak areas gathered from chromatographic traces. As an example of a conventional method that utilizes a mass spectrometer with ionization source and mass analyzer(s) as previously described (U.S. Pat. No. 6,906,320 B2 and US 2018/0011990 A1), data is acquired using filters to include specific m/z values that correspond to the target analyte, a small number of anticipated metabolites, and the internal standard. Peak areas for those ions are extracted from selected ion chromatograms (SIC) and quantified relative to a calibration curve as an expression of time-dependent exposure. Based on those, PK parameters could be calculated, such as exposure ($C_{max}$), time of $C_{max}$ ($t_{max}$), half-life ($t_{1/4}$), and area under the curve (AUC).

Another example of a conventional method that utilized multiple reaction monitoring (MRM) for quantitative purposes by selecting only a few metabolites to monitor for SIC peak area extraction is described in US 2004/0181347 A1. The MRM analysis is limited due to the limitations of a mass spectrometer; it is not practical to use selective ion monitoring for every possible analyte. Besides, SICs are generated manually (or with previously saved profiles generated manually) within the instrument software.

While the previously described methods are useful for the structural analysis of biomolecules, the analytical techniques, software and visualization tools are independent of each other and do not offer a comprehensive analysis of all the various spectra. The available software is too rigid and lacks open source needs with very limited application programming interfaces (API's). Additionally, the steps to identify the biomolecule from the various spectra are often meticulous and time consuming with no capabilities for high throughput screening (HTS).

For at least the limitations described above there is a need for a system that generates pharmacokinetic analyses of oligonucleotide total effects from full-scan mass spectra.

BRIEF SUMMARY OF THE INVENTION

One or more embodiments described in the specification are related to a system that generates pharmacokinetic analyses of oligonucleotide total effects from full-scan mass spectra. The system automates and simplifies many of the steps in a pharmacokinetic analysis that are typically manual and repetitive.

One or more embodiments of the system analyze sample data from experimental administration of an oligonucleotide (such as an ASO or siRNA) to an organism, such as a human or animal model. Samples collected at different times are analyzed by a mass spectrometer that generates full-scan spectra of the samples. A processor receives the full-scan spectra and analyzes the data to calculate the total concentration of the therapeutically active substances in the samples.

A user may input the molecular sequence of the oligonucleotide. The user may also provide a maximum nucleotide loss from the oligonucleotide that maintains pharmacological activity. The system may calculate a set of active metabolites from the oligonucleotide based on this maximum nucleotide loss. The user may also input a charge envelope expected for the molecules of interest, and the system may calculate the mass-to-charge ratios for the active molecules from this data. The sum of the relative intensities of the full-scan spectra at these mass-to-charge ratios may be used to calculate the total concentration of the active molecules at each point in time, and one or more pharmacokinetic parameters may be calculated from the time series of total active molecule concentrations.

Pharmacokinetic parameters may include for example concentration (exposure), elimination constants, clearance, half-life, and area under the curve. (Concentration may be viewed as an input into pharmacokinetic modeling, from which other parameters are calculated; in this specification we include any measure of concentration or exposure within the term "pharmacokinetic parameter.") In one or more embodiments calculation of these parameters fit a one-compartment or two-compartment model to the curve of active molecule concentration over time. Data may be analyzed to determine whether a one-compartment or two-compartment model is appropriate, and then the parameters may be calculated using corresponding sets of equations for either a one-compartment or a two-compartment model.

In one or more embodiments, samples may include a known concentration of an internal standard. Mass spectra intensities may be compared to the intensity of the internal standard to generate relative intensities. Total relative intensities of active molecules may be compared to one or more calibration curves to calculate the total active molecule concentration at each point in time.

In one or more embodiments, the set of active molecule mass-to-charge ratios may be calculated by calculating the molecular weight of each active molecule (the parent oligonucleotide or an active metabolite), subtracting a charge times the atomic mass of a proton, and dividing by the charge. The charge may vary within a charge envelope provided by the user. A range of mass-to-charge ratios may be generated for each active molecule mass-to-charge ratio by adding or subtracting an error value.

In one or more embodiments, a set of metabolite nucleotide sequences may be calculated by removing nucleotides from one or both ends from the parent oligonucleotide, up to a maximum number of nucleotides. A set of conjugated metabolites may be calculated by removing one or more molecules conjugated to the oligonucleotide sequence, such as GalNAc for example. The set of active metabolites may be calculated as combinations of the metabolite nucleotide sequences and the conjugate metabolites.

In one or more embodiments, full scan spectra may be filtered so that only metabolites having at least a threshold number of peaks are included in the sum of active molecule relative intensities.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A system that generates pharmacokinetic analyses of oligonucleotide total effects from full-scan mass spectra will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

One or more embodiments of the invention may be used to analyze the pharmacokinetics of an oligonucleotide, such as for example an antisense oligonucleotide (ASO) or a small interfering RNA (siRNA). While these oligonucleotides are a significant focus of the invention, one or more embodiments of the invention may be used with any type of molecule or molecules, including but not limited to nucleotide-based therapies containing RNA or DNA fragments.

Figure 1:
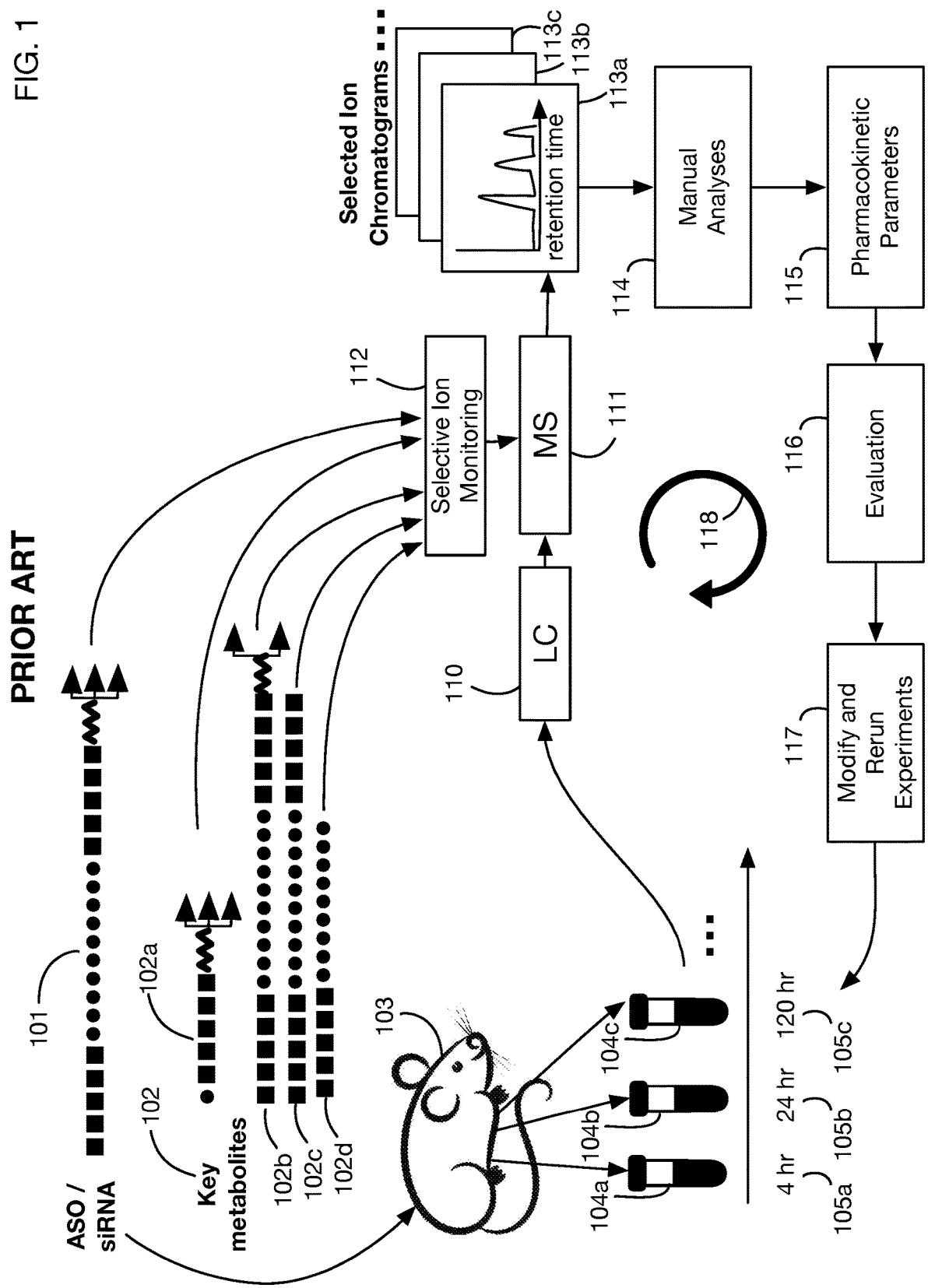
FIG. 1 illustrates typical steps used in the prior art to perform a pharmacokinetic analysis of an oligonucleotide; steps are generally manual and experiments may need to be repeated several times.

FIG. 1 shows typical steps used in the prior art to investigate the pharmacokinetics of an oligonucleotide 101. The oligonucleotide may for example consist of a sequence of nucleotides, shown in FIG. 1 as squares (for nucleotides that have been artificially modified) and circles (for unmodified nucleotides). It may also have a conjugation such as GalNAc or Tocopherol linked to either end, shown in FIG. 1 as a GalNAc conjugation depicted as a tail with three triangles. To analyze the pharmacokinetics of this molecule 101, it is administered to an organism 103, which may be a human or an animal model, and samples such as 104a, 104b, and 104c are taken from the organism at a series of times 105a, 105b, and 105c. Typically multiple organisms will be used for a single experiment to provide replicates. The samples will then be analyzed to determine the concentration of the molecule 101 over time, and these concentrations will be used to develop pharmacokinetic analyses. Analysis of the samples for concentration of the molecule 101 may for example use liquid chromatography 110 coupled with mass spectrometry 111.

In many situations, the molecule 101 will be metabolized by the organism 103 into metabolites, and one or more of these metabolites may also be of interest for the pharmacokinetic analysis. Metabolites may be of interest because they also have significant pharmacological effects. This situation is particularly relevant for oligonucleotides, because these molecules often remain effective even when several nucleotides are removed from the ends of the sequence. In addition, the conjugations added to the oligonucleotides may also be metabolized, which modifies the molecule but does not necessarily impact efficacy. For these reasons, analysis of an oligonucleotide is typically more complex than simply analyzing the samples 104a, 104b, 104c for the concentration of the original molecule 101 over time.

Generally an analyst will therefore identify a set of key metabolites 102 prior to conducting a pharmacokinetic experiment. Analysis of the samples will then search for the original molecule 101 as well as the key metabolites 102. Illustrative metabolites 102 include metabolite 102a with nucleotides removed from the left end of the original molecule 101, metabolite 102b with a portion of the GalNAc conjugate removed, metabolite 102c with all conjugation and linker removed, and metabolite 102d with the conjugation and linker removed as well as additional nucleotides removed from the right end. In current practice in the art, concentrations of each of these substances is determined using selective ion monitoring 112. This process uses the molecular formulas of each molecule of interest to program the mass spectrometer 111 to search specifically for the mass-to-charge ratios expected for ions resulting from each molecule. While selective ion monitoring 112 can result in mass spectra acquired with greater sensitivity, a tradeoff is that it requires up front identification of the metabolites of interest 102.

The result of the LC/MS analyses using selective ion monitoring 112 is typically a series of selected ion chromatograms 113a, 113b, 113c corresponding to the sample times 105a, 105b, 105c. These chromatograms are then analyzed manually in step 114 to generate pharmacokinetic parameters 115. These manual analyses may take several days for each experiment. They may also require a mass spectrometrist who is highly skilled in spectral analysis. Results are then evaluated in step 116. If additional data is needed, or if results are unacceptable, modifications 117 may be made and experiments may be rerun. Since selective ion monitoring 112 was used to collect data, in particular any search for different metabolites will require a completely new experiment to collect new data that includes those metabolites. The feedback loop 118 for the entire pharmacokinetic analysis may therefore be very time-consuming and expensive.

Figure 2:
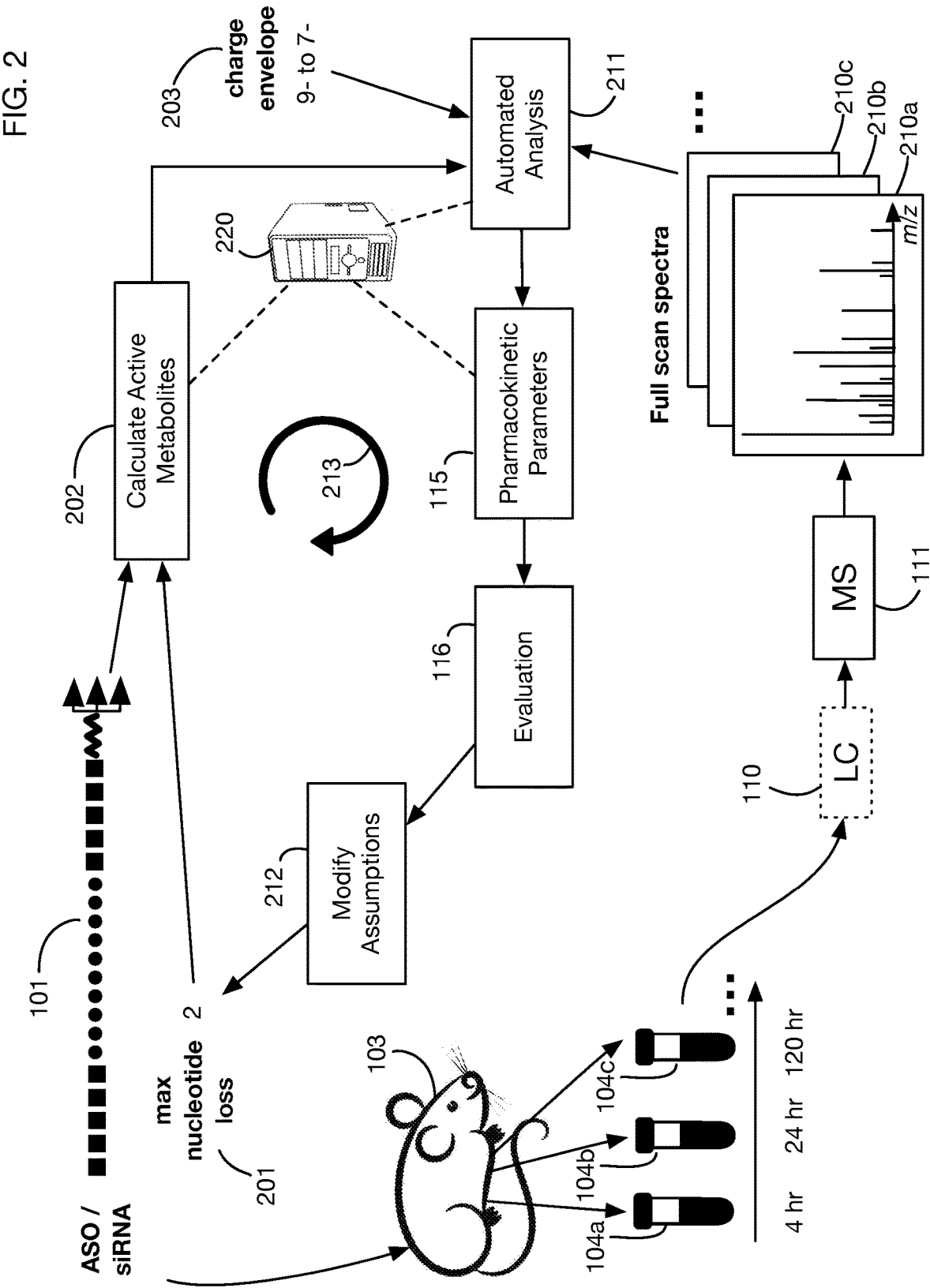
FIG. 2 shows illustrative steps in an embodiment of the invention; analyses are highly automated and provide the flexibility to vary assumptions without repeating experiments.

FIG. 2 shows illustrative steps enabled by one or more embodiments of the invention. In comparison to the typical process in the prior art shown in FIG. 1, these steps are simpler, faster, and highly automated. In addition, the process shown in FIG. 2 provides considerable flexibility in modifying analyses without repeating entire experiments and collecting new samples. As described with respect to FIG. 1, an oligonucleotide 101 is administered to an organism 103 and samples 104a, 104b, and 104c are collected at a series of times. These samples are analyzed with mass spectrometer 111, and often with a front end chromatography stage 110 as well to aid in molecule separation. Instead of explicitly identifying metabolites of interest, as shown for example as metabolites 102 in FIG. 1, a user identifies only the maximum number of nucleotides 201 that can be lost from molecule 101 (on one or both ends) that maintains the desired efficacy of the therapy. The system then performs calculation 202 to determine the possible metabolites from the parent molecule 101. This calculation 202, as well as other calculations and analyses described below, may be performed using one or more processors 220, which may be for example, without limitation, a desktop computer, a laptop computer, a server, a smart phone, a tablet, a notebook computer, or a network or combination of any of these devices. A user may also provide a charge range 203 for the expected charge envelope of the ions of molecule 101 and its metabolites; this data may be available from previous mass spectra, for example, or may be based on analysis of the possible ionizations of the molecules. For oligonucleotides, the ions in a mass spectrometer will typically be negative.

The mass spectrometer 111 generates full scan spectra for each sample, such as spectrum 210a for sample 104a, spectrum 210b for sample 104b, and spectrum 210c for sample 104c. Use of full scan spectra represents a significant departure from the prior art process illustrated in FIG. 1, which typically uses the mass spectrometer with selective ion monitoring. A key benefit of using full scan spectra is that all potential metabolites are captured in the spectra, instead of those that are pre-identified by the analyst before using the mass spectrometer. The full mass spectra are then automatically analyzed in step 211. This analysis generates a total concentration for the oligonucleotide and for all metabolites calculated in step 202. Details of this analysis are described below. The automated analyses may be performed on the processor or processors 220. The system may then calculate one or more pharmacokinetic parameters 115 from the time series of concentrations. Evaluation 116 of the results may lead to modified assumptions 212. Unlike the process shown in FIG. 1, different assumptions may not require that the experiment be repeated; instead because full scan spectra are available, different analyses may be performed on the same data. The feedback loop 213 may therefore be considerably shorter and less expensive. For example, an analyst may modify the maximum nucleotide loss 201 and repeat the analysis without collecting any additional data.

Figure 3:
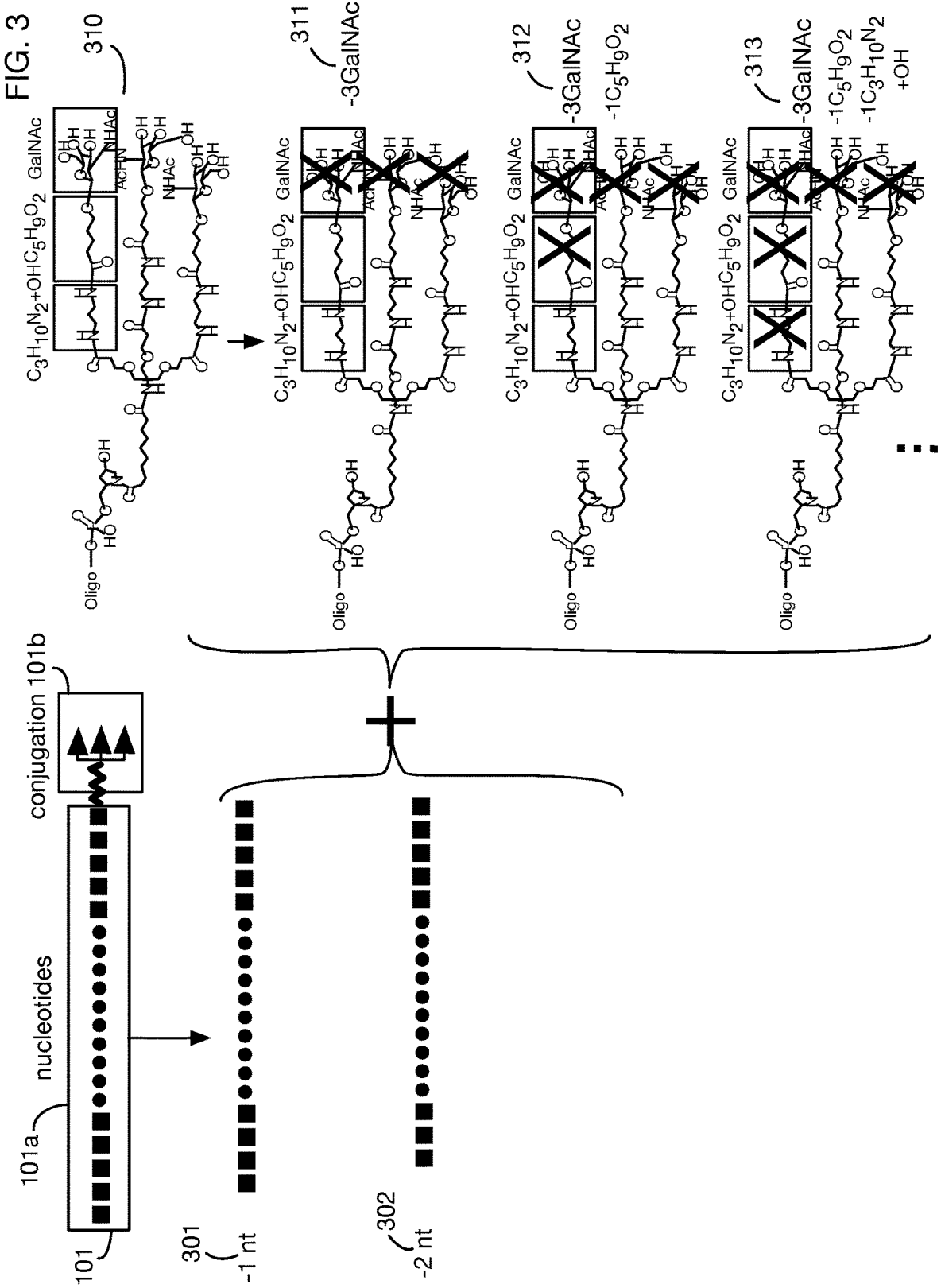
FIG. 3 illustrates automated calculation of metabolite molecular formulas from a parent oligonucleotide.

FIGS. 3 through 7 illustrate details of the steps shown in FIG. 2. FIG. 3 illustrates step 202 of calculating active metabolites. One or more embodiments of the system may include chemistry modules that can identify how molecule 101 may break into parts under the biologic conditions in organism 103. These modules may for example model the effects of enzymes or reactions on the molecule. In particular, in one or more embodiments, products from the nucleotides portion 101a and the conjugation portion 101b of molecule 101 may both be modeled. The nucleotides portion products may be based on the maximum nucleotide loss 201 provided by the user. Nucleotides may be removed from one or both ends of the molecule. However, when a conjugation is present on one end of the oligonucleotide, such as the GalNAc conjugation 101b shown in FIG. 3, nucleotides cannot be removed from that end unless the entire conjugation is also removed. Thus in this example nucleotide sequence 101a may generate subsequences 301 or 302, with a loss of at most 2 nucleotides from left end of the molecule. Products of the conjugation component 101b may also be modeled, for conjugates that are metabolized. FIG. 3 shows an illustrative conjugate 310, which is a triple N-Acetylgalactosamine (GalNAc). As molecule 101 is metabolized, portions of this conjugate 310 may be removed; illustrative products are shown as modified conjugates 311, 312, and 313. In one or more embodiments, a full set of metabolites may be generated by combining all combinations of nucleotide subsequences (such as 301 and 302) and conjugate subsets (such as 311 through 313). Some conjugations, such as Tocopherol for example, may remain unmodified in metabolites, in which case only the nucleotide loss (from the other side) may be modeled.

Figure 4:
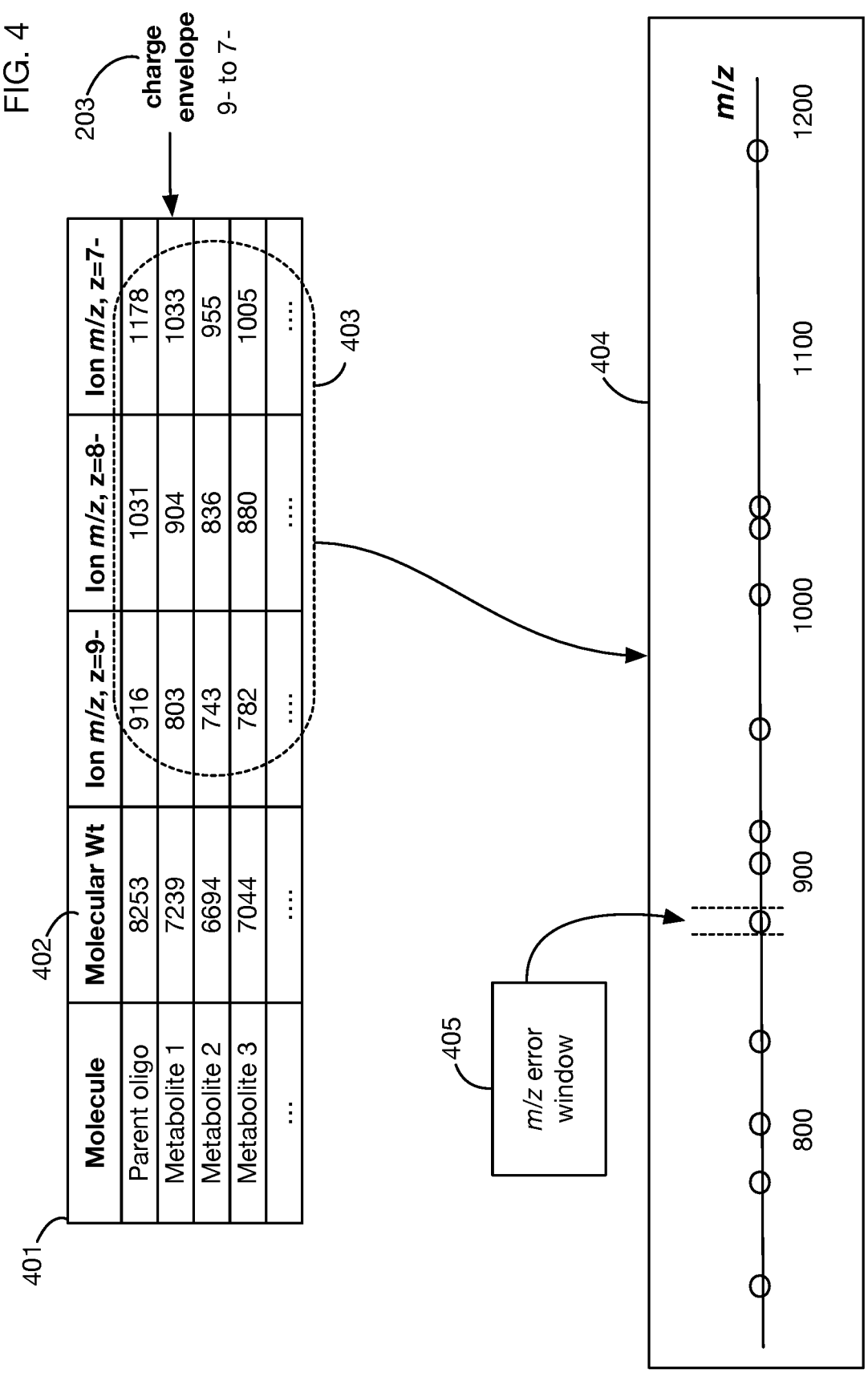
FIG. 4 show illustrative calculation of mass-to-charge ratios for an oligonucleotide and its metabolites.

Once a complete set of presumed active molecules is calculated, which consists of the original oligonucleotide and the active metabolites such as those illustrated in FIG. 3, a subsequent step in one or more embodiments is to determine the mass-to-charge ratios that these active molecules may have in the mess spectra. This process is illustrated in FIG. 4. The system calculates entries in table 401 for each active molecule. The molecular weight 402 of each molecule is calculated directly from its molecular formula. Based on the range 203 of possible charges expected for the ions of these molecules, a set 403 of possible ion mass-to-charge (m/z) ratios is determined. For negative ions, the mass-to-charge of an ion will be the molecular weight of the molecule minus the charge times the molecular weight of a proton, divided by the charge. For some molecules, isotopes may exist with slightly different molecular weights. However, relatively low resolution mass spectra may be used, which will have minimal isotopic peaks. In one or more embodiments, a background subtraction with a blank may be performed prior to analyzing the mass spectra, which increases the quality of peak picking by eliminating the matrix signal, and also reduces high resolution spectra (which may have isotopic peaks present) to low resolution (with minimal isotopic peaks).

The combination of all possible m/z ratios 403 for the active molecules generates a screen 404 for mass-to-charge ratios to consider in the mass spectra. An error window 405 may be generated around each value to take into account mass spectrometer resolution or other noise; this window 405 contains m/z values in the range of the calculated ion mass-to-charge ratio plus or minus an error value.

Figure 5:
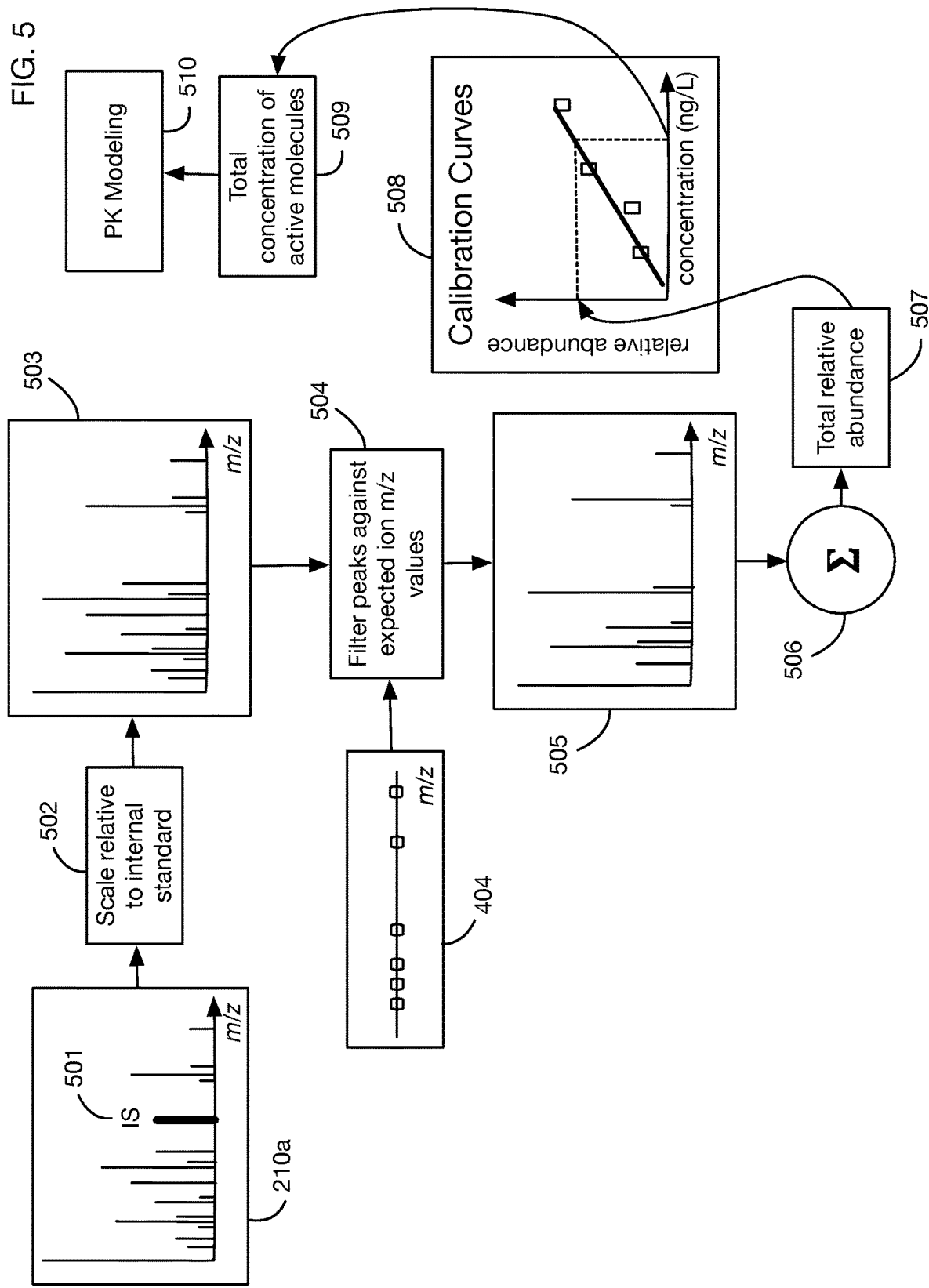
FIG. 5 illustrates steps used in one or more embodiments of the invention to process mass spectra automatically to generate pharmacokinetic analyses.

This mass-to-charge screen 404 may then be applied to the full scan spectra to complete the analysis, as shown in FIG. 5. Associated with each mass spectrum such as spectrum 210a is an intensity 501 of an internal standard that is added to each sample in a known concentration. The spectrum 210a may then be scaled in step 502 relative to the summed intensity 501 of the internal standard, to yield rescaled spectrum 503. In step 504 the peaks of this rescaled spectrum are then filtered against the mass-to-charge filter 404, to yield filtered peaks 505. The relative intensity of each of these filtered peaks may then be summed in step 506 to provide a measure of the total relative abundance 507 of all active molecules in the sample. This total relative abundance 507 may then be compared to one or more calibration curves 508 that relate the mass spectrum relative abundance to the concentration of the molecules in the sample. The resulting total concentration 509 of all active molecules may then be used in pharmacokinetic modeling 510 for the total effect of the therapy.

In one or more embodiments, the scaling relative to the internal standard may be performed after filtering 504 and summing 506, instead of prior to filtering and summing as shown in FIG. 5. The resulting total relative abundance will be identical with either approach. Scaling after filtering and summing is illustrated below in FIG. 6.

Figure 6:
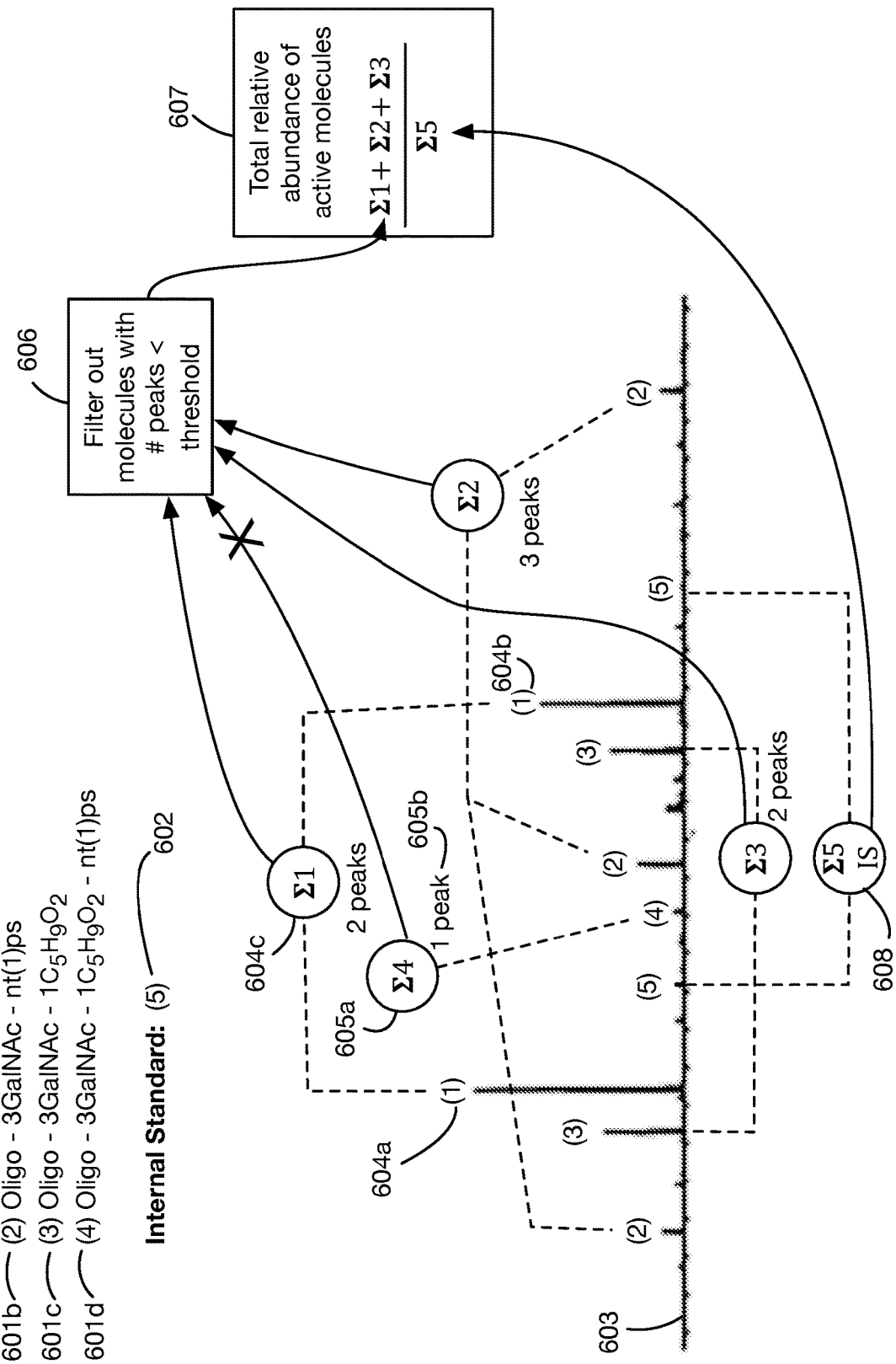
FIG. 6 shows an illustrative oligonucleotide sequence and selected metabolites, and illustrates a mass spectrum associated with these molecules.

FIG. 6 illustrates the analysis of a realistic mass spectrum for a set of four active molecules 601a through 601d. (In this example the original oligonucleotide is not included, because at least a portion of the conjugated GalNAc molecules will be removed by metabolism.) Products 601a through 601d may be calculated for example using a process similar to that shown in FIG. 3. An internal standard 602 is added to each sample. Mass spectrum 603 has several peaks, and some of these correspond to possible m/z ratios for the molecules 601a through 601d. Some peaks also correspond to the internal standard 602. For example, peaks 604a and 604b correspond to ions of molecule 601a. The peaks associated with each of the molecules are summed; for example, sum 604c is the sum of peaks 604a and 604b. In one or more embodiments, these peak sums may be further filtered in step 606 to ensure that at least a minimum number of peaks are present for the associated molecule. For example, if a metabolite is expected to show two or three peaks in spectrum 603, but only one is present, then the system may determine that the peak likely does not correspond to the molecule, and this peak may be excluded from the sum. In the illustrative spectrum 603, there is only a single peak corresponding to molecule 601d. If the number of peaks threshold is 2, for example, then this peak count 605b associated with this molecule 601d will cause the sum 605a to be excluded via filter 606. The remaining peaks may then be summed in step 607, and may then be divided by the sum 608 for the internal standard 602, to yield the total relative abundance 607 of the active molecules relative to the internal standard.

Figure 7:
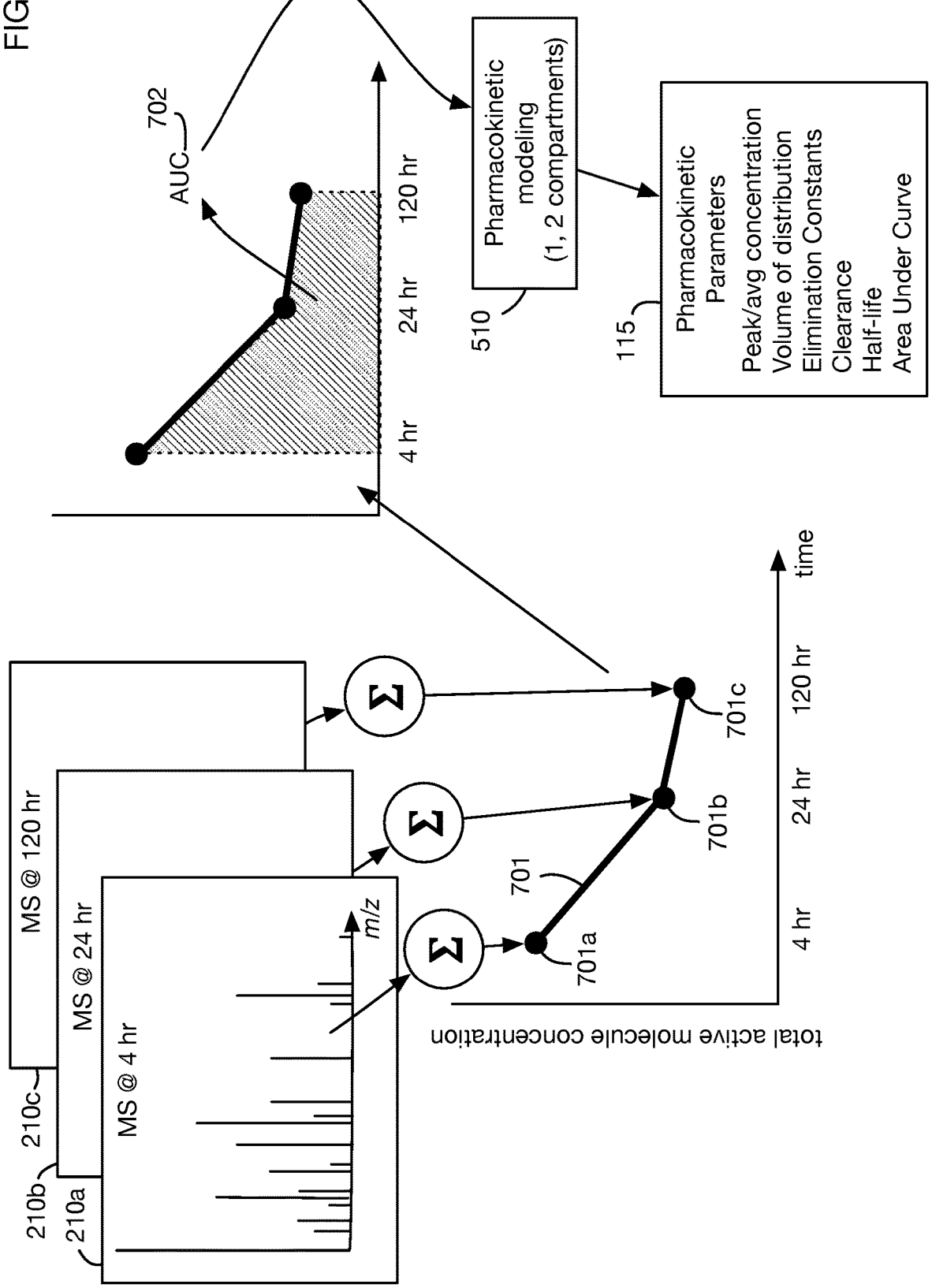
FIG. 7 illustrates generation of pharmacokinetic models and parameters from a time sequence of mass spectra.

FIG. 7 illustrates calculation of pharmacokinetic parameters and models from the analyzed mass spectra data. Peaks in the time series of mass spectra 210a, 210b, and 210c are filtered, summed, and scaled, as described above, to yield a time series 701 of total concentrations of active molecules. This time series may then be analyzed to calculate pharmacokinetic parameters, such as for example an area under the curve 702, which may be calculated directly by numerically integrating curve 701 between desired limits. (For example, a trapezoidal approximation may be used to calculate the integral under the curve.) Other parameters such as parameters 115 may be calculated by fitting one or more models 510, such as one-compartment or two-compartment models, to data 701. For one and two compartment models, the remaining parameters 115 may be calculated from the area under the curve 702. For example, clearance can be calculated from the area under the curve and the dose (which is known); volume of distribution can be calculated from dose and concentration (which can be extrapolated from the curve); elimination rate constants can be calculated from volume of distribution and clearance; and half-life can be calculated from elimination rate constants.

While the invention herein disclosed has been described by means of specific embodiments and applications thereof, numerous modifications and variations could be made thereto by those skilled in the art without departing from the scope of the invention set forth in the claims.

What is claimed is:

1. A system that generates pharmacokinetic analyses of oligonucleotide total effects from full-scan mass spectra, comprising:
   a processor comprising memory that includes software configured to
      receive full-scan spectra from a mass spectrometer of a series of samples taken from one or more organisms at a corresponding series of times after administration of an oligonucleotide;
      accept user input comprising
         a molecular sequence of said oligonucleotide;
         a maximum nucleotide loss from said oligonucleotide that maintains pharmacologic activity; and
         an oligonucleotide charge envelope of said oligonucleotide in said mass spectrometer;
      calculate a set of active metabolites of said oligonucleotide based on said molecular sequence of said oligonucleotide and on said maximum nucleotide loss;
      calculate an active metabolite charge envelope associated with each active metabolite of said set of active metabolites;
      calculate a set of active molecule mass-to-charge ratios based on
         said molecular sequence of said oligonucleotide;
         said oligonucleotide charge envelope;
         said set of active metabolites; and
         said active metabolite charge envelope associated with each active metabolite of said set of active metabolites;
      calculate a total active molecule concentration at each time of said series of times,
         wherein said total active molecule concentration at said each time is based on a sum of relative intensities of said full-scan spectra at said each time across said set of active molecule mass-to-charge ratios; and,
      calculate one or more pharmacokinetic parameters from said total active molecule concentration at each time of said series of times.

2. The system of claim 1, wherein said one or more pharmacokinetic parameters comprise one or more of concentration, elimination constants, clearance, half-life, and area under the curve.

3. The system of claim 2, wherein said calculate said one or more pharmacokinetic parameters comprises fit a one-compartment model or a two-compartment model to a curve of said total active molecule concentration at each time of said series of times.

4. The system of claim 1, wherein
said processor is further configured to receive one or more calibration curves associated with said mass spectrometer;
said series of samples comprise a known concentration of an internal standard;
said relative intensities of said full-scan spectra comprise measured intensities in said full-scan spectra divided by an intensity of said internal standard in said full-scan spectra; and
said calculate said total active molecule concentration at each time of said series of times comprises
compare said sum of relative intensities to said one or more calibration curves to obtain said total active molecule concentration at said each time.

5. The system of claim 1, wherein said set of active molecule mass-to-charge ratios comprises a union of
for each oligonucleotide charge in said oligonucleotide charge envelope,
a molecular weight of said molecular sequence of said oligonucleotide minus said each oligonucleotide charge times a proton molecular weight, divided by said each oligonucleotide charge, plus or minus an error value; and,
for each active metabolite of said set of active metabolites, and for each active metabolite charge in said active metabolite charge envelope associated with said each active metabolite,
a molecular weight of said each active metabolite minus said each active metabolite charge times a proton molecular weight, divided by said each active metabolite charge, plus or minus said error value.

6. The system of claim 1, wherein said calculate a set of active metabolites of said oligonucleotide comprises
calculate a set of metabolite nucleotide sequences by removing at most said maximum nucleotide loss from said oligonucleotide on one or both ends of said oligonucleotide;
calculate a set of conjugate metabolites from one or more molecules conjugated to nucleotides of said oligonucleotide; and,
calculate said set of active metabolites as combinations of said set of metabolite nucleotide sequences and said set of conjugate metabolites.

7. The system of claim 1, wherein said total active molecule concentration at said each time is further based on a sum of relative intensities of said full-scan spectra at said each time across a subset of said set of active molecule mass-to-charge ratios corresponding to molecules having a number of peaks in said full-scan spectra that exceeds a threshold number of peaks.

8. A system that generates pharmacokinetic analyses of oligonucleotide total effects from full-scan mass spectra, comprising:
a processor comprising memory that includes software configured to
receive full-scan spectra from a mass spectrometer of a series of samples taken from one or more organisms at a corresponding series of times after administration of an oligonucleotide, wherein said series of samples comprise a known concentration of an internal standard;
receive one or more calibration curves associated with said mass spectrometer;
accept user input comprising
a molecular sequence of said oligonucleotide;
a maximum nucleotide loss from said oligonucleotide that maintains pharmacologic activity; and
an oligonucleotide charge envelope of said oligonucleotide in said mass spectrometer;
calculate a set of active metabolites of said oligonucleotide based on said molecular sequence of said oligonucleotide and on said maximum nucleotide loss, comprising
calculate a set of metabolite nucleotide sequences by removing at most said maximum nucleotide loss from said oligonucleotide on one or both ends of said oligonucleotide;
calculate a set of conjugate metabolites from one or more molecules conjugated to nucleotides of said oligonucleotide; and
calculate said set of active metabolites as combinations of said set of metabolite nucleotide sequences and said set of conjugate metabolites;
calculate an active metabolite charge envelope associated with each active metabolite of said set of active metabolites;
calculate a set of active molecule mass-to-charge ratios that comprises a union of for each oligonucleotide charge in said oligonucleotide charge envelope,
a molecular weight of said molecular sequence of said oligonucleotide minus said each oligonucleotide charge times a proton molecular weight, divided by said each oligonucleotide charge, plus or minus an error value; and,
for each active metabolite of said set of active metabolites, and for each active metabolite charge in said active metabolite charge envelope associated with said each active metabolite,
a molecular weight of said each active metabolite minus said each active metabolite charge times a proton molecular weight, divided by said each active metabolite charge, plus or minus said error value;
calculate a total active molecule concentration at each time of said series of times, wherein said total active molecule concentration at said each time is based on
a sum of relative intensities of said full-scan spectra at said each time across a subset of said set of active molecule mass-to-charge ratios corresponding to molecules having a number of peaks in said full-scan spectra that exceeds a threshold number of peaks, wherein said relative intensities comprise measured intensities in said full-scan spectra divided by an intensity of said internal standard in said full-scan spectra; and
a comparison of said sum of relative intensities to said one or more calibration curves; and,
fit a one-compartment model or a two-compartment model to a curve of said total active molecule concentration at each time of said series of times to calculate one or more pharmacokinetic parameters, wherein said one or more pharmacokinetic parameters comprise one or more of concentration, elimination constants, clearance, half-life, and area under the curve.

* * * * *